United States Patent [19]

Kortenbach et al.

[11] Patent Number: 5,242,461
[45] Date of Patent: Sep. 7, 1993

[54] VARIABLE DIAMETER ROTATING RECANALIZATION CATHETER AND SURGICAL METHOD

[75] Inventors: Juergen A. Kortenbach, Ft. Lauderdale; John W. Box, Miami, both of Fla.

[73] Assignee: Dow Corning Wright, Arlington, Tenn.

[21] Appl. No.: 734,366

[22] Filed: Jul. 22, 1991

[51] Int. Cl.⁵ .............................................. A61B 17/32
[52] U.S. Cl. .................................... 606/159; 606/170; 606/180
[58] Field of Search ............... 606/159, 170, 180, 171; 15/104.14; 604/22

[56] References Cited

U.S. PATENT DOCUMENTS

| | | | |
|---|---|---|---|
| 4,811,735 | 3/1989 | Nash | 128/305 |
| 4,895,560 | 1/1990 | Papantonakos | 604/22 |
| 4,966,604 | 10/1990 | Reiss | 606/170 |
| 5,041,124 | 8/1991 | Kensey | 606/170 |

FOREIGN PATENT DOCUMENTS

| | | | |
|---|---|---|---|
| 0117519 | 2/1984 | European Pat. Off. | 606/159 |
| 3732236 | 12/1988 | Fed. Rep. of Germany | 606/159 |

Primary Examiner—G. Fred Rosenbaum
Assistant Examiner—W. Lewis
Attorney, Agent, or Firm—John L. Chiatalas; Robert L. McKellar

[57] ABSTRACT

According to the invention there is provided an intravascular catheter comprising an elongated flexible jacket having opposed proximal and distal ends and a central passageway extending between and interconnecting the ends. A rotating working head is located at the distal end of the jacket. A flexible drive cable extends through the passageway of the jacket, having a driving end operatively connected to the working head for rotating it, and a driven end operatively connected to a high-speed motor. The working head is rotatably mounted in a bearing sleeve which is further attached to the catheter jacket. The working head is actuated, by a actuator which adjust the a pair of tip portions from an at least initial retracted position with a first effective working diameter to an extended position with a second effective working diameter greater than the first effective diameter. Centrifugal forces generated by rotation of the cable cause the tip portions to assume the greater effective working diameter.

13 Claims, 2 Drawing Sheets

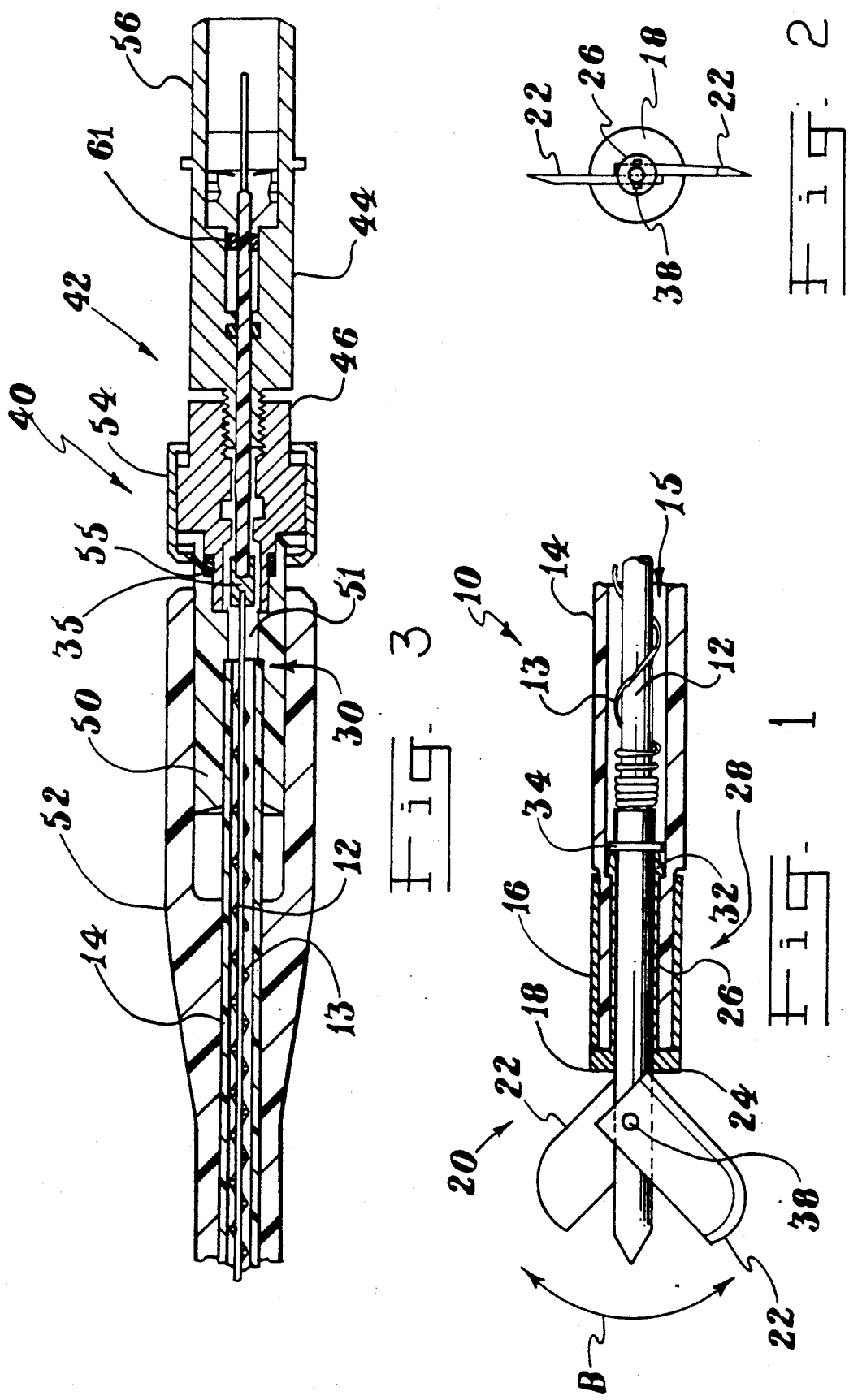

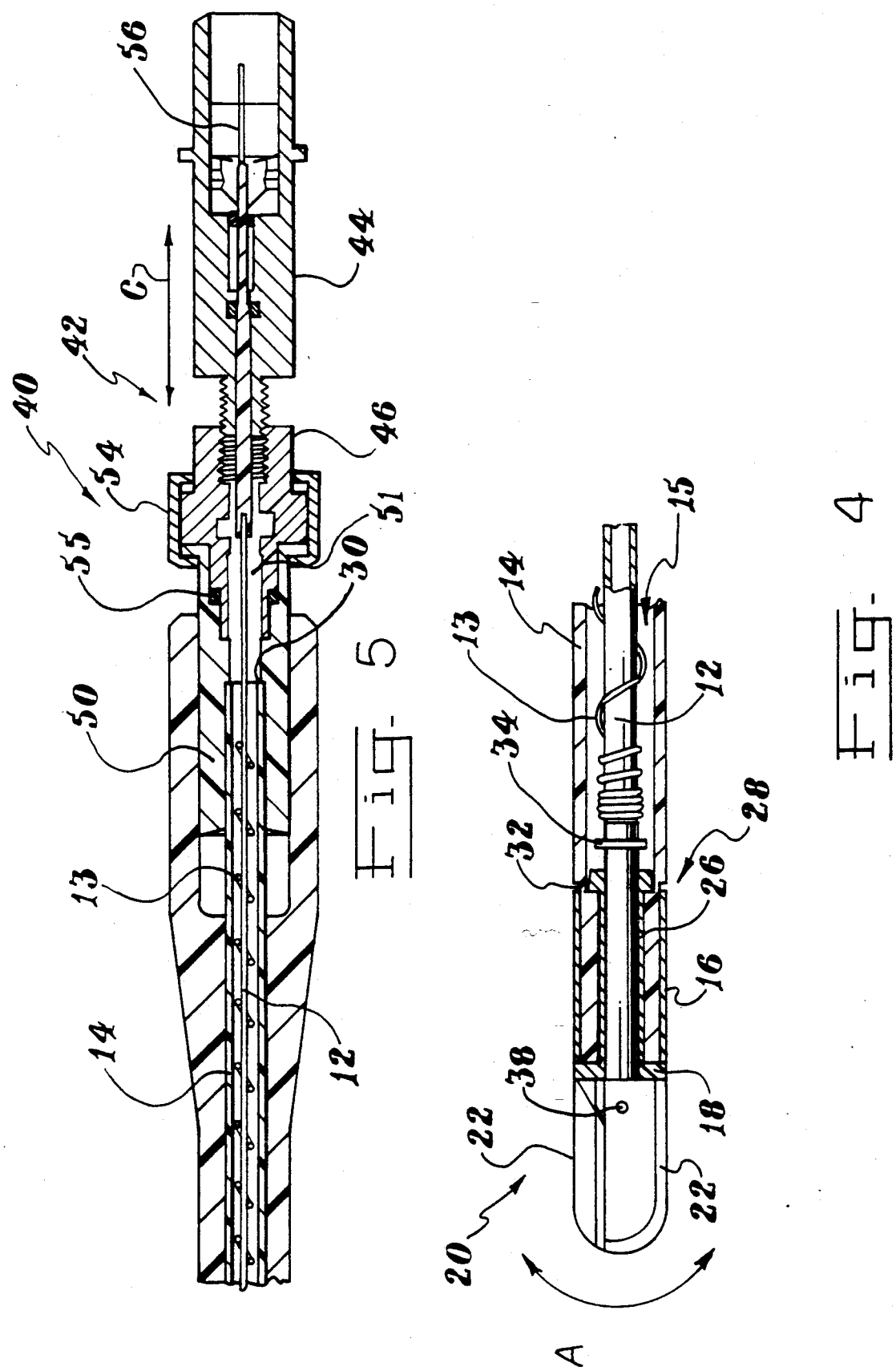

VARIABLE DIAMETER ROTATING RECANALIZATION CATHETER AND SURGICAL METHOD

TECHNICAL FIELD

The invention generally relates to a catheter useful in removing occlusions from a vessel, particularly an artery or vein.

BACKGROUND OF THE INVENTION

During an intravascular procedure, it is typically necessary to utilize some type of mechanical device to remove an occlusion from a vessel. Generally a recanalization catheter including a rotatable working head with a fixed diameter is used for engaging and cutting the blockage from the vessel wall. As the catheter is advanced, the vessel increases or decreases in diameter necessitating the use of several different tip sizes to complete the procedure. Fixed diameter catheters of this type are available from Dow Corning Wright-Theratek, under the name "TRAC-WRIGHT", in various size designations.

To change the working diameter during the procedure, the catheter is removed from the lumen of the vessel and a catheter having a larger or smaller working diameter corresponding to the changed lumen diameter is reinserted into the vessel.

U.S. Pat. No. 4,895,560 to Papantonakos describes a milling tool for angioplasty comprising an actuator cylinder for increasing or decreasing the diameter of the tool. The tool further comprises a multiplicity of flexible, leaf-shaped flutes axially connected to a driving rod. The flutes are linearly displaceable with respect to the actuator cylinder, causing a change in the radial dimension of the flutes. As the rod is retracted by the actuator through a base plate the tool is compressed, forcing the flutes to bow outward thereby increasing the effective working diameter of the tool a corresponding amount. One disadvantage of this tool is that sharpened edges of the rotating flutes can damage vascular tissue.

U.S. Pat. No. 4,811,735 to Nash describes a catheter for destroying gallstones within the body. The catheter is positioned adjacent a stone to pulverize it on contact when the working head is rotated. The working head comprises several pivotally mounted impacting arms radially arrayed at the end of a drive shaft that is said to rotate at high speeds from 5,000 to 100,000 rpm. The centrifugal force of rotation urges the pivotally attached arms to move from a retracted position to an extended position, thus striking the stone and disintegrating it. The catheter utilizes centrifugal force to cause the hammers to pulverize the stones, rather than scraping to remove occlusions from a vessel.

Accordingly, there remains a need for a rotating catheter which is expandable to different working diameters and non-cutting to vascular tissue having varying lumen sizes.

SUMMARY OF THE INVENTION AND ADVANTAGES

According to the invention there, is provided an intravascular catheter comprising an elongated flexible jacket having opposed proximal and distal ends, defining a central passageway extending between the ends. A working head is located at the distal end of the jacket. A flexible drive cable extends through the central passageway, including a driving end rotatably connected to the working head and a driven end operatively connected to a power source for rotating the working head. An actuator is provided for actuating the working head from at least an initial retracted position having a first effective working diameter to an extended position having a second effective working diameter greater than the first working diameter. Centrifugal forces generated by rotation of the cable cause the working head to assume the greater second working diameter.

An advantage of the invention is the safe removal of an occlusion by scraping the vessel wall with a non-cutting tool.

Another advantage of the invention is the capability of adjusting the effective diameter of the working head to accommodate various lumen sizes without removal of the catheter from the vessel.

Accordingly, it is a general objective of this invention to provide a method for performing a medical/surgical procedure using the invention, while overcoming disadvantages of the prior art.

BRIEF DESCRIPTION OF THE DRAWINGS

The invention may be better appreciated by reference to the attached drawings, which illustrate one or more preferred embodiments, wherein:

FIG. 1 is a sectional view of the working head of the catheter according to the invention;

FIG. 2 is an end view of FIG. 1;

FIG. 3 is a sectional view of the actuator with the tip portions in the extended position;

FIG. 4 is a sectional view of the working head of the catheter with the tip portions in the retracted position;

FIG. 5 is a sectional view of the actuator with the tip portions in the retracted position.

Further objects and advantages can be appreciated by reference to the ensuing detailed description, taken in conjunction with the above mentioned drawings, wherein the reference numerals are used to designate corresponding structures of the drawings.

DETAILED DESCRIPTION OF ONE OR MORE PREFERRED EMBODIMENTS

Referring in general to FIG. 1, an intravascular catheter is generally shown at 10, for removing occlusions from a vessel. With further reference to FIG. 1, the catheter 10 has a flexible drive cable 12 extending within central passageway 15 between the proximal 30 and distal 28 ends of the catheter jacket 14. The driven end 35 of drive cable 12 (FIG. 3) is attached to an actuator 40 which is further attached to the drive means (not shown) to rotate the cable 12 at high speeds. The working head generally indicated at 20 is located at the distal end 28 of the catheter jacket 14, and includes a pair of tip portions 22 mounted to pivot as the working head is rotated by the cable 12. The actuator 40 actuates the working head 20 for adjusting the tip portions 22 from an at least initial retracted position A (FIG. 4) having a first effective working diameter, to an extended position B (FIG. 1) having a second effective diameter greater than the first working diameter. The position of tip portions 22 change due to centrifugal forces generated by the rotation of cable 12, resulting in the tip portions assuming a greater effective working diameter.

Referring to FIG. 1, the working head 20 further comprises a shaft 26 at the driving end of the cable 12. The tip portions 22 are pivotally mounted on the shaft 26 by a pin 38 and separable from one another by centrifugal force as the cable 12 rotates the shaft at high-speeds. The outside of shaft 26 is inserted into a bearing sleeve 18 and a weld collar 34 is affixed to the outside diameter of the shaft. The bearing sleeve 18 including a barbed end 32 and the shaft 26 are further inserted into the jacket 14 and a crimp band 16 crimped around the jacket circumference forming a press-fit which permanently affixes the shaft and bearing sleeve to the working head 20, while still allowing the shaft to rotate freely within the bearing sleeve. The barbed end 32 further retains the bearing sleeve within the jacket 14. The bearing sleeve 18 also presents a bearing face in contact with the shoulder 24 of the tip portions 22 when the tip portions are in a retracted position. The cable 12 is made of small diameter tubular wire and is further surrounded by an elongated helically-wound bearing 13. The helically-wound bearing 13 takes the form of a wire coil surrounding the cable 12 and prevents the rotating cable from frictionally contacting the internal surface of the jacket 14 when the jacket is bent, as bending often occurs in conforming to the vessel curvature.

It will be appreciated by those skill in the art that catheters could have a hollow drive cable, i.e., a drive cable that is not solid but hollow and which includes a central opening aligned with a guideway formed in the drive shaft of the present catheter. Thus, a conventional guidewire could be passed through an opening to facilitate placement of the catheter at the desired arterial site. Such an embodiment could also incorporate infusion and aspiration means.

Referring to FIGS. 3 and 5, the actuator 40 further comprises a tensioning mechanism 42 having a male portion 44 threadedly engaging a female portion 46. The tensioning mechanism 42 further comprises a drive insert 50 containing proximal end 30 of the jacket 14, and both the jacket and drive insert are enclosed by jacket boot 52. A drive housing 54 couples the drive insert 50 including a swivel O-ring 55 to the female portion 46. The driven end 35 of the flexible drive cable 12 is welded to a drive pin 56, and the drive pin further extends through central channel 51 of the tensioning mechanism 42 and terminates within the male portion 44. The drive pin 56 is restrained from moving in the axial direction within the male portion 44 as the male portion is rotated. A shaft O-ring 61 forms a seal around drive pin 56 and central channel 51.

The tensioning mechanism 42 increases the working diameter of the tip portions 22 by extending the shaft 26 distally within bearing sleeve 18 and decreases the working diameter of the tip portions by retracting the shaft proximally.

As the male portion 44 is rotated counterclockwise the threads of the female portion 46 are disengaged, moving the male portion a distance C and moving the drive pin 56 in the proximal direction thereby moving drive cable 12 in the same direction since the drive pin and drive cable are attached. When the male portion 44 is rotated in the clockwise direction the threads of the female portion 46 are engaged thereby moving the drive pin 56 in the distal direction further resulting in the shaft 26 moving distally within bearing sleeve 18. The travel of shaft 26 in the distal direction is limited by the spacing between the weld collar 34 and the barbed end 32 of sleeve 18. As the shaft 26 extends distally, the weld collar 34 comes into contact with the barbed end 32 preventing over-extension of the working head 20 relative to distal end 28 of jacket 14.

Referring again to FIGS. 3 and 5, the actuator 40 is responsible for advancing cable 12 distally, to increase the distance between the shoulders 24 of the tip portions 22 and the front face of bearing sleeve 18 allowing the tip portions to separate freely, in response to the centrifugal forces exerted during rotation, thus expanding to a larger effective cutting diameter. As the cable 12 is retracted proximally by actuator 40, the shoulders 24 of the tip portions are forced against the front face of bearing sleeve 18, thereby decreasing the effective cutting diameter of the tip portions 22. The actuator 40 advances and retracts the cable 12, while having a drive means (not shown) coupled to pin 56 through the tensioning mechanism 42. The tip portions 22 can have an infinite number of effective working diameters dependent upon the number of threads that are engaged on the tensioning mechanism 42.

In operation, the working head 20 of the catheter 10 is inserted percutaneously through an incision into the vessel, then progressively advanced to the location of the occlusion or blockage. The tip portions 22 are rotated, the working head 20 further advanced until engaging and removing the occlusion from the vessel wall by the scraping non-abrasive action.

That which is claimed is:

1. An intravascular catheter for removing occlusions from a vessel comprising:
   (a) an elongated flexible jacket having opposed proximal and distal ends, defining a central passageway extending between the ends;
   (b) a working head located at the distal end of the jacket;
   (c) a flexible drive cable extending through the central passageway, including a driving end rotatably connected to the working head at the proximal end and a driven end operatively connected to a power source for rotating the working head, the working head having a shaft operatively connected to the drive cable at the distal end of the jacket, including a pair of tip portions pivotally mounted on the shaft, the tip portions being separable from one another by centrifugal forces as the shaft rotates; and
   (d) a actuator for actuating the working head from at least an initial retracted position having a first effective working diameter to an extended position having a second effective working diameter greater than the first effective diameter whereby centrifugal forces generated by rotation of the cable cause the tip portions to assume the greater second working diameter.

2. The catheter of claim 1 wherein the working head further comprises a rotating tip, including a sleeve presenting a bearing face which axially contacts a distal shoulder of the working head in a retracted position.

3. The catheter of claim 2 wherein the sleeve permanently affixes the shaft to the working head.

4. The catheter of claim 3 wherein the sleeve radially engages the external surface of the shaft.

5. The catheter of claim 4 wherein the actuator moves the drive cable distally to space the tip portions further away from the bearing face allowing the tip to rotate freely and moves proximally to retract the tip, positioning the shoulders of the tip closer to the bearing face thereby decreasing the effective cutting diameter of the tip.

6. The catheter of claim 5 further comprising a tensioning mechanism for actuating the pair of tip portions.

7. The catheter of claim 6 wherein the tensioning mechanism increases the effective cutting diameter by extending the flexible drive cable and decrease the effective cutting diameter by retracting the flexible drive cable.

8. The catheter of claim 7 wherein the tensioning mechanism is rotatable in one direction to extend the flexible drive cable or in an opposite direction thereby retracting the cable to cause axial movement of the shaft within the bearing sleeve.

9. The catheter of claim 5 wherein the drive means is coupled to the cable through the tensioning mechanism.

10. The catheter of claim 1 wherein the proximal end of the drive cable is rotatably coupled to the drive means.

11. A method for removing occlusions from a vessel comprising the steps of:
 (a) inserting the catheter of claim 1 into a incision made in the vessel;
 (b) advancing the working head of the catheter near the site of the occlusion;
 (c) rotating the working head and further advancing the working head to contact the occlusion with the rotating tip portions, thereby scraping the occlusion from the vessel wall.

12. An intravascular catheter for removing occlusions from a vessel comprising:
 (a) an elongated flexible jacket having opposed proximal and distal ends, defining a central passageway extending between the ends;
 (b) a working head located at the distal end of the jacket comprising a shaft, a pair of rotating tip portions, a sleeve presenting a bearing face which axially contacts a distal shoulder of the working head in a retracted position, the tip portions being pivotally mounted on the shaft, and separable from one another by centrifugal forces as the shaft rotates;
 (c) a flexible drive cable extending through the central passageway, including a driving end rotatably connected to the shaft at the distal end of the jacket and a driven end operatively connected to a power source for rotating the shaft; and
 (d) a actuator for actuating the working head from at least an initial retracted position having a first effective working diameter to an extended position having a second effective working diameter greater than the first effective diameter whereby centrifugal forces generated by rotation of the cable cause the tip portions to assume the greater second working diameter.

13. An intravascular catheter for removing occlusions from a vessel comprising:
 (a) an elongated flexible jacket having opposed proximal and distal ends, defining a central passageway extending between the ends;
 (b) a working head located at the distal end of the jacket comprising a shaft, a pair of rotating tip portions, a sleeve presenting a bearing face which axially contacts a distal shoulder of the working head in a retracted position, the tip portions being pivotally mounted on the shaft, and separable from one another by centrifugal forces as the shaft rotates;
 (c) a flexible drive cable extending through the central passageway, including a driving end rotatably connected to the shaft at the distal end of the jacket and a driven end operatively connected to a power source for rotating the shaft; and
 (d) a actuator for actuating the working head from at least an initial retracted position having a first effective working diameter to an extended position having a second effective working diameter greater than the first effective diameter, by causing the shaft to move axially in a distal and proximal direction within the sleeve when the flexible drive cable is actuated, whereby centrifugal forces generated by rotation of the cable cause the tip portions to assume the greater second working diameter.

* * * * *